… … … … … … … … … … … … … … … … … … … …

United States Patent [19]
Polin et al.

[11] Patent Number: 5,261,898
[45] Date of Patent: Nov. 16, 1993

[54] TEMPORARY COLOSTOMY APPARATUS

[76] Inventors: Stanton G. Polin, 8620 N. Keeler Ave., Skokie, Ill. 60076; Melvin I. Eisenberg, 3849 Swanson Ct., Gurnee, Ill. 60031

[21] Appl. No.: 611,764
[22] Filed: Nov. 13, 1990
[51] Int. Cl.$^5$ .............................................. A61F 5/44
[52] U.S. Cl. .................................. 604/328; 606/192; 604/327; 604/332
[58] Field of Search .............. 604/100, 327, 328, 332, 604/338, 339, 29, 31, 192; 600/29, 31; 606/192; 623/11

[56] References Cited
U.S. PATENT DOCUMENTS

| | | | |
|---|---|---|---|
| 3,828,782 | 8/1974 | Polin | 604/328 |
| 3,988,782 | 11/1976 | Dardik et al. | 623/11 |
| 4,117,846 | 10/1978 | Clayton | 604/328 |
| 4,248,235 | 2/1981 | Taylor | 604/100 |
| 4,555,242 | 11/1985 | Saudagar | 606/192 |

Primary Examiner—David Isabella
Assistant Examiner—Rob Clarke
Attorney, Agent, or Firm—Jerome Goldberg

[57] ABSTRACT

A temporary colostomy apparatus for diverting the fecal stream and comprising an open ended excrement tube including a fecal receiving end having a liquid inflatible balloon on the outside thereof. A dissolvable and absorbable band is snugly wrapped around the outside of the colon at a preselected location. The tube is inserted inside the colon through a slit opening, so that the balloon is further inward but adjacent the band. The balloon is inflated so that the outer circular periphery thereof contacts the inside surface of the arrested colon and has a circumference slightly larger than the band. The inflated balloon and the band are in an abutting relationship with a common area of the colon sandwiched therebetween, to prevent outward movement of the tube. A retainer ring is positioned on the disposal end of the tube and pressed against the outside of the body to prevent inward movement of the tube. A disposable bag is secured to the disposal end of the tube on the outside of the body for collecting the fecal stream fully diverted into the receiving end of the tube. The colon is sutured to the abdominal wall adjacent the surgical openings in the colon and abdomen, to further stabilize the position of the tube inside the colon. When normal colon and rectal bowel functions could be resumed and prior to any substantial dissolving of the band, the balloon is deflated and the excrement tube is removed from the colon. The band remains encircled around the colon and in time the band is dissolved, absorbed and excreted from the body.

22 Claims, 4 Drawing Sheets

TEMPORARY COLOSTOMY APPARATUS

BACKGROUND OF THE INVENTION

This invention relates generally to a colostomy apparatus for evacuating fecal matter, and more particularly relates to a temporary colostomy apparatus for totally diverting the fecal stream.

A colostomy is a vent in the colon for the purpose of evacuating fecal matter and gas. Depending upon the patient's specific condition, the colostomy may be permanent or temporary. A temporary colostomy can be constructed to partially or totally divert the fecal stream.

In the past, a colostomy generally required that the bowel be extended out from an abdominal incision. A colostomy pouch usually supported by a belt or girdle was kept constantly in position to receive the fecal matter discharged during the colostomy. This arrangement is extremely objectionable due to the frequent escapage of foul odors and leakage of the fecal matter onto the body and wearing apparel. Sometimes instead of a belt or girdle, the colostomy bag was fixidly positioned against the outside of the abdominal wall with an adhesive. The adhesive often caused irritation, which chafed or maserated the abdominal skin.

U.S. Pat. No. 3,838,782

In U.S. Pat. No. 3,838,782 (1974) entitled "Temporary Colostomy Tube", an improved device and method were disclosed for overcoming the aforedescribed objectionable previous means for temporarily diverting the fecal stream. The prior colostomy device included an open ended excrement tube having an inflatible balloon secured on the fecal receiving end of the tube.

A non-absorbable band was wrapped around the outside of the colon at a selected location. The tube was inserted in the colon so that the balloon was further inward but adjacent the band.

The balloon was inflated with air to provide a circumference slightly larger than the band and together with the tube occupied the entire vertical space inside the colon. The inflated balloon abutted the band with a common portion of the colon sandwiched therebetween.

A retainer ring was positioned on the disposal end of the tube and pressed against the outside of the body. A disposal bag was fastened around the tube disposal opening for collecting the fecal matter. When normal colon and rectal bowel functions could be resumed, the balloon would be deflated and the excrement tube removed from the colon. The band would not be removed from inside the body and would remain wrapped around the colon.

The material of such prior band was not dissolvable inside the body, but was formed from material known not to react adversely in the body. To remove the band, another operation would be required—causing undesirable additional stress and shock to the body of the patient.

Surgeons and professional persons involved with colostomies appreciated the improvement of my prior temporary colostomy device, but, nevertherless heretofore, have been reluctant to consider use of my prior improved device with humans. They were primarily concerned with the possibility of future unforeseen problems that could arise from the permanent retention inside the body of the band around the outside of the colon. This objection has been overcome by the invention herein which provides a band that dissolves and is absorbed and excreted from the body, after the excrement tube is no longer necessary for diverting the fecal stream and had been removed from the body.

In the prior colostomy tube device, the air inflated balloon inside the colon would partially deflate over time to produce movement and instability of the excrement tube inside the colon. This would cause seepage of the fecal stream around the periphery of the balloon and consequently the fecal stream was not fully diverted inside the tube. To solve this problem, liquid is preferably used for inflating the balloon. As an additional safeguard against premature deflating of the balloon, a one way valve is positioned inside the liquid flow pathway to prevent any liquid back flow out from the balloon.

Another defect of the prior temporary colostomy tube device was the possibility that the neck of the disposal bag on the outside of the body would fold or twist to the side and press against the planar circular edge at the disposal end of the excrement tube to form a closal seal and block outflow of the fecal stream. The fecal stream unable to find a flow path into the disposal bag would build up sufficient pressure around the outside of the balloon to cause seepage into the surgically sore areas in the colon or bowel, thereby increasing the liklihood of infection. To overcome this, spaced notches are formed in the outer edge at the disposal end of the excrement tube, to prevent the formation of a seal against fecal flow by the disposal bag.

Moreover, an alternate disposal bag without a neck portion is provided which snaps on to the disposal end of the excrement tube, thereby minimizing any possibility that the bag itself would form a closure across the disposal opening of the tube.

SUMMARY OF INVENTION

The primary object of the invention herein is to provide a temporary colostomy apparatus for fully diverting the fecal stream during the period required for the bowel or the colon, as the case may be, to sufficiently heal after surgery.

A primary feature of the invention herein is to provide a dissolvable band for snugly wrapping around the outside of the colon and abutting an inflated balloon secured to the outer surface of an excrement tube and positioned inside the colon. A common portion of the colon is sandwiched between the balloon and the band. After the sore and tender area of the colon or bowel has sufficiently healed following surgery to normally function and receive the fecal stream, the internal balloon is deflated and the excrement tube is pulled out from inside the colon. The band is left wrapped around the outside of the colon after the excrement tube has been removed. Thereafter, the band fully dissolves and is absorbed and excreted from the body. The absorbable band may be formed from a polyglycolic acid mesh known also as DEXON PGA mesh, or a vicryl knitted mesh known also as Polyglactin 910.

Another feature of the invention is to inflate the internal balloon secured to the receiving end of the excrement tube with liquid. A related feature is to provide a one way valve positioned in the liquid flow path to the internal balloon to permit liquid to flow into the balloon but prevent back flow of fluid out from the internal balloon.

Another feature of the invention is to suture the portion of the colon adjacent the slit opening in the colon for receiving the excrement tube, to the abdominal wall adjacent to the incision made in the abdomen, to prevent appreciable colon movement.

Still another feature is to provide a monitoring external balloon on the outside of the body which inflates simultaneously with the internal balloon, and deflates simultaneously with the internal balloon, to thereby sense when the excrement tube is not diverting the fecal stream.

Still another feature is to provide a trocar removably positioned in the receiving end of the excrement tube to provide an opening through the muscles of the abdomen having substantially the same cross-sectional area as the excrement tube.

Still another feature is to provide grooves in the disposal end of the excrement tube to afford a flow path for the fecal stream into the disposal bag, in the event the main outlet from the disposal end of the tube is blocked from the twisting or folding of the neck of the disposal bag to the side of the person instead of hanging downward.

Yet another feature is to provide a retainer ring having elongated slits cut through the thickness of the ring to provide ease in twisting or turning the retainer ring for securing the excrement tube to the outside of the body and prevent inward movement of the tube inside the colon.

Still another feature is to provide a flexible retainer ring having a circular reduced thickness area adjacent the ring opening, to afford increased flexibility when turning or twisting the ring in position against the outside of the abdomen of the patient for securing the excrement tube.

Still another feature is to provide a trocar for removably positioning in the opening at the receiving end of the excrement tube and having a circular lip for protectively covering the circular edge of the deflated balloon adjacent to the opening of the tube.

BRIEF DESCRIPTION OF THE DRAWINGS

Referring to the drawing in which the same characters of references are employed to indicate corresponding similar parts throughout the several Figures of the drawing.

DESCRIPTION OF PREFERRED EMBODIMENT

Figures 1, 2, 3, 4:
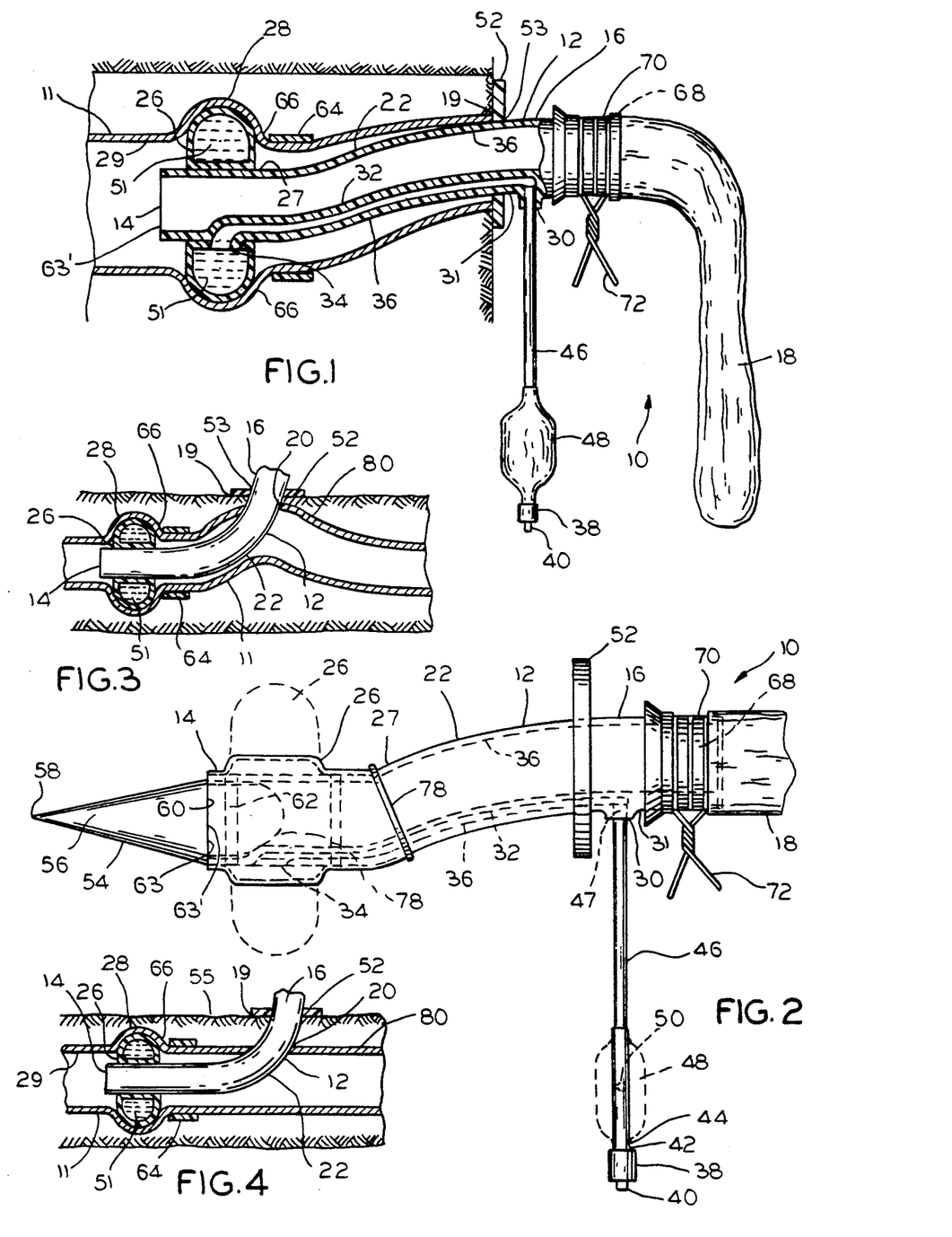
FIG. 1 is a sectional side front view of the temporary colostomy apparatus operatively positioned in the body, and embodying the principles of the invention.
FIG. 2 is a side view of the excrement tube and showing the trocar removably positioned in the receiving end of the excrement tube.
FIG. 3 is a schematic sectional top view of the temporary colostomy apparatus positioned inside the body (showing variation in the structure of the excrement tube for convenience of illustration) and showing the colon sutured to the abdominal wall.
FIG. 4 is a schematic sectional top view of the temporary colostomy apparatus positioned inside the body (similar to FIG. 3) prior to suturing the colon to the abdomen.
Figures 5, 6, 7:
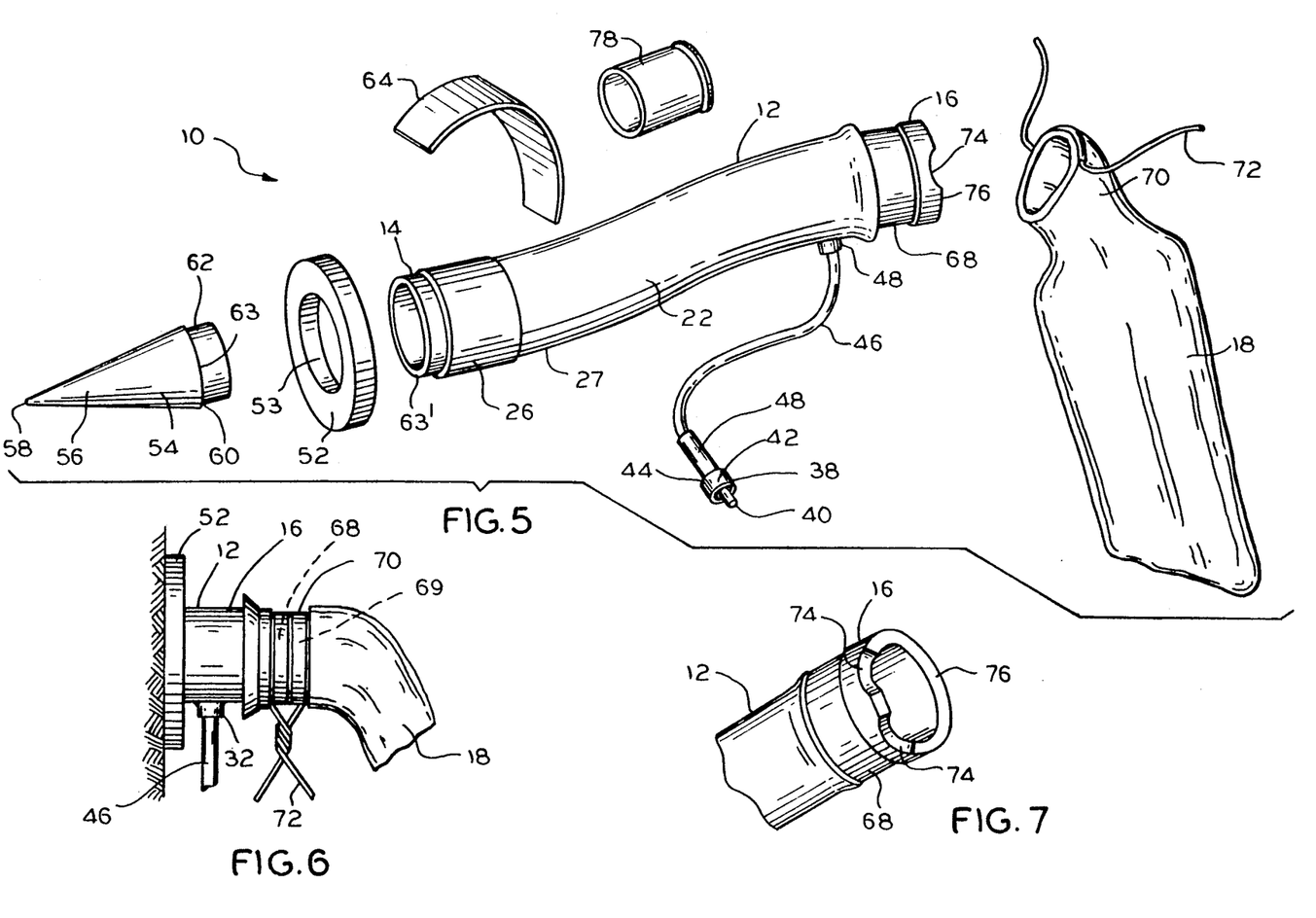
FIG. 5 is a perspective view of the various parts of the temporary colostomy apparatus spaced apart.
FIG. 6 is a fragmentary side view of the disposal end of the excrement tube with the disposal bag attached and the retainer ring pressed against the body of the patient.
FIG. 7 is a fragmentary perspective view of the disposal end of the excrement tube and showing the grooves formed in the outer edge thereof.

Referring now to FIGS. 1, 2 and 5 of the drawings, the reference numeral 10 indicates generally a temporary colostomy tube apparatus for inserting into the colon 11 of the large intestine of the patient. Generally, the colostomy tube apparatus 10 would be positioned in the transverse colon or in the sigmoid colon.

The colostomy tube apparatus 10 includes a hollow open ended excrement tube 12 for positioning inside the colon and diverting the fecal stream. The excrement tube 12 has a receiving end 14 to receive the fecal stream for passage through the tube 12 to the opposite or disposal end 16 for flowing into a disposal or colostomy bag 18. The tube 12 is rigid in construction and formed from a plastic material. Silastic plastic (a Dow Corning product) may be used to construct the tube 12, but other type materials which do not harmfully react inside the body may also be suitable. An incision 19 is formed in the abdominal wall and a slit 20 is cut through a selected site on the colon. The excrement tube 12 is passed through the incision 19 in the abdomen and the slit 20 in the colon 11 for positioning inside the colon.

As further viewed in FIGS. 1, 2 and 3, the intermediate portion 22 of the excrement tube 12 is inclined in an upward direction and integrally connects the receiving end 14 with the disposal end 16 of the tube 12. The tube 12 may have a substantially "S" configuration. The receiving end 14 and the disposal end 16 extend substantially horizontally as viewed in FIGS. 1 and 2, but the disposal end 16 is at a raised vertical level as compared with the receiving end 14 when the tube 12 is operatively positioned inside the colon 11.

An inflatable internal balloon 26 formed of an elastic plastic or rubber material, is fused to the outside surface 27 of the excrement tube 12 at the receiving end 14 of the tube. The internal balloon 26 has substantially a doughnut shape and fully occupies the space between the tube 12 and the inside surface of the colon. The inflated balloon 26 provides a slight circular bulge 28 around the arrested colon 11 (FIG. 1) as it makes circular contact with the inside surface 29 of the colon. The tube 12 and inflated balloon 26 completely block the fecal stream and fully divert the fecal stream into the receiving end 14 of the tube 12.

An inlet opening 30 is formed in the bottom wall 31 at the disposal end 16 of the excrement tube 12. An elongated hollow and narrow internal tubular member 32 extends from the inlet opening 30 to the inside of the internal balloon 26. The tubular member 32 includes an outlet opening 34 aligned with an opening into the inside of the internal balloon 26 for inflating the balloon. The tubular member 32 is fused to the inside surface 36 of the tube 12.

A one way valve 38 includes an input end 40 and an output end 42 attached to an inlet end 44 of an external tubular member 46. The outlet end 47 of the external tubular member 46 is secured inside the inlet opening 30 to the internal tubular member 32 and in communication therewith. An external monitoring balloon 48 is positioned around the external tubular member 46 and sealed thereto.

An aperture 50 is formed in the external tubular member 46 aligned with an opening to the inside of the external balloon 48, to inflate the external balloon 48 simultaneously with the inflating of the internal balloon 26. The external balloon 48 functions as a monitor to determine whether the internal balloon 26 is still inflated. If the internal balloon 26 deflates prematurely the external monitor balloon 48 will also be deflated, to indicate malfunction of the temporary colostomy tube apparatus 10 and probable passage of the fecal stream into the sore and unhealed areas of the colon or bowel.

The external balloon 48 is substantially smaller than the internal balloon 26. The aperture 50 in the external tubular member 46 has an area appreciably less than the cross sectional area of the external tubular member 46, so that the smaller external balloon 48 will inflate at approximately the same rate as the larger internal balloon 26.

Liquid 51 is preferably used for inflating the internal balloon 26. Air could also be used but an air inflating system requires extremely tight sealing of the flow passageways to prevent leakage and premature deflating of the internal balloon 26 during the use of the temporary colostomy tube apparatus 10. The one way valve 38 may be forced open with the nozzle of a syringe (not shown) for passage of fluid to inflate the internal balloon 26 and the external monitoring balloon 48, and automatically closes when the nozzle is removed. The valve 38 is again manually opened to drain the fluid out from the system for deflating the internal balloon prior to the removal of the excrement tube 12 from the body of the patient.

A pliable resilient retainer ring or washer 52 is formed with a central opening 53 having a diameter just slightly larger than the outside diameter of the excrement tube to afford a tight and secure association with the tube.

The retainer ring 52 is initially placed on the receiving end 14 of the tube 12 and moved along the tube to its normal position at the disposal end 16 adjacent to and inward from the liquid inlet opening 30. The tightening of the retainer ring 52 against the body of the patient prevents the excrement tube 12 from moving inward inside the colon.

A trocar 54 is removably press fitted inside the receiving end 14 of the excrement tube 12. The trocar includes a conical portion 56 having a sharply pointed outer end 58. The conical portion 56 increases in cross sectional area from the point 58 to a circular shoulder 60. An annular neck portion 62 spaced inward from the outer edge 63 of the shoulder 60 protrudes outward therefrom. The outside diameter of the neck portion 62 is just slightly less than the inside diameter of the receiving end 14 of the tube 12. The circumference of the outer edge 63 is substantially the same as the outside diameter of the tube 12. As may be seen from FIG. 2, the neck 62 of the trocar 54 press fits inside the receiving end 14 of the tube 12 with the shoulder 60 abutting the outer edge 63' of the receiving end 14 of tube 12.

After the incision 19 is made in the abdominal wall of the patient, the trocar 54 is thrust through the incision and the layers of abdominal muscle to form the proper sized opening for inserting the excrement tube 12. The tube 12 is passed through the slit 20 in the colon and a purse string suture is formed around the tube 12.

A band 64 is wrapped around the outside of the colon 11 inside the body of the patient. The band 64 is a length of material dimensioned to snugly encircle the arrested colon after the opposite free ends are sutured or otherwise secured together. The band 64 may slightly depress the colon at the selected site.

The band 64 is positioned about 1½ inches or two inches inward from the slit 20 in the colon 11 so that the band 64 lies between the slit 20 and the internal balloon 26 after the excrement tube 12 has been placed inside the colon 11. The balloon 26 is inflated with liquid 51 and then the excrement tube is pulled outwardly away from the patient so that the inflated balloon 26 is adjacent the band 64 in a substantially abutting relationship with a common circular section 66 of the colon 11 sandwiched therebetween.

The band 64 is formed from a soluble and absorbable material, which dissolves after the colostomy tube apparatus 10 is no longer being used by the patient and the excrement tube 12 has been removed from the colon. The dissolved material is absorbed and excreted from the body. The band 64 starts dissolving approximately three to five weeks after inserted into the body.

Thus, after about 21 days the band 64 cannot be dependent upon to provide the abutting surface with the internal balloon 26, for preventing movement of the tube 12 toward the abdominal incision. If the band 64 does not provide a firm or fixed surface, the balloon may oscillate or otherwise move to cause seepage of fecal matter into the sore colon or bowel area. Therefore, the fecal stream would no longer be fully diverted into the excrement tube.

To minimize or prevent fecal seepage, particularly in the event the band prematurely dissolves prior to sufficient healing of the colon or bowel area, the horizontal length of the inflated balloon should be greater than the inside diameter of the arrested colon where the tube 12 is inserted.

Figure 19:
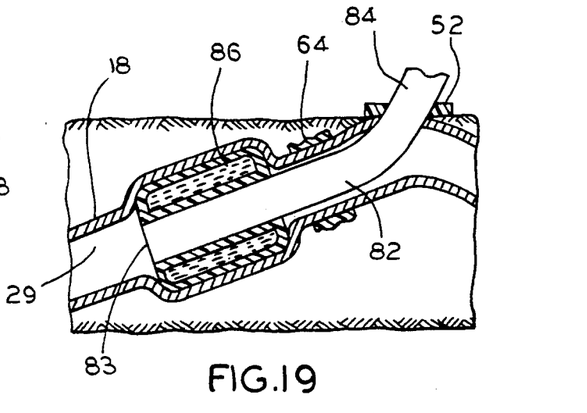
FIG. 19 is a schematic sectional top view of the temporary colostomy apparatus and showing the excrement tube angled inside the colon with the inflated tubular balloon maintaining the receiving end of the tube in the pathway of the fecal stream.

Moreover, the larger horizontal length of the inflated balloon is a safeguard against the receiving end 14 of the tube 12 from shifting ninety degrees so that it lies against the inside surface of the colon, to thereby cause blockage of the fecal stream instead of diverting the fecal stream. This feature is further discussed when describing the embodiments in FIGS. 8, 17 and 19.

An absorbable polyglycolic acid (PGA) mesh may be used for the material for the band 64. This material may be referred to as DEXON PGA Mesh. DEXON is a registered trademark of American Cyanamid. A vicryl knitted mesh referred to as Polyglactin 910 may also be suitable for the dissolvable material for the band 64. The vicryl knitted mesh material is made by ETHICON, a division of Johnson & Johnson.

The suture material securing the band around the colon may be conventional dissolvable sutures, which are also dissolved, absorbed and excreted from the body.

An annular depression 68 is formed in the disposal end 16 of the tube 12 (FIGS. 1,2 and 5). The neck 70 of the disposal bag 18 is inserted over the depression 68 and the tie strings 72 are attached together and compresses the neck 70 of the bag 18 inside the depression 68.

As may be seen from FIGS. 5 and 7, arcuate concave grooves 74 are formed in the outermost edge 76 of the disposal end 16 of the tube 12. The grooves 74 afford a path way for the fecal stream, in the event the neck 70 of the disposal bag 18 bends laterally or bunches together across the opening out at the disposal end 16 of the tube. Thus, the grooves 74 provide a path for the fecal stream into the bag 18 even if the primary flow path out from the disposal end 16 of the tube 12 may be closed.

A cylindrical, flexible sleeve or sheath 78 (FIGS. 2 and 5) may be positioned or rolled over the excrement tube 12 to protect the internal balloon 26 from puncturing or being damaged when the tube 12 is being stored and also particularly when the trocar 54 is being used. After the trocar 54 is removed from the receiving end 14 of the tube 12, the sleeve 78 is pulled or rolled off the receiving end 14 of the tube, and thereafter the tube is operatively inserted inside the colon 11.

The cooperation of the inflated internal balloon 26 with the band 64 prevents the outward movement of the excrement tube 12. The cooperation of the retainer ring 52 with the tube 12 prevents inward movement of the balloon 26 away from the band 64.

To further stabilize the position of the temporary colostomy tube apparatus 10 inside the body, the anterior surface 80 of the colon adjacent the slit 20 is sutured to the abdominal wall (FIGS. 1 and 3) adjacent to the incision 19 in the abdomen, to prevent disruptive movement of the colon 11 which could cause undesirable movement of the internal balloon 26. Thus, the fixed position of the colostomy tube 12 inside the body prevents seepage of the fecal matter past the inflated balloon 26 and into the surgically cut and unhealed areas in the colon or bowel.

Moreover, the suturing of the colon to the abdominal wall shortens the distance of the fistula which forms between the colon and the abdominal wall. Thus, the fistula track is formed sooner, is stronger, and more compact than it would be if the colon were not sutured to the abdominal wall. The compact fistula prevents the portion of the colon adjacent the incision 19 from moving and tearing away from the abdominal wall during peristalsis.

Figures 8, 9:
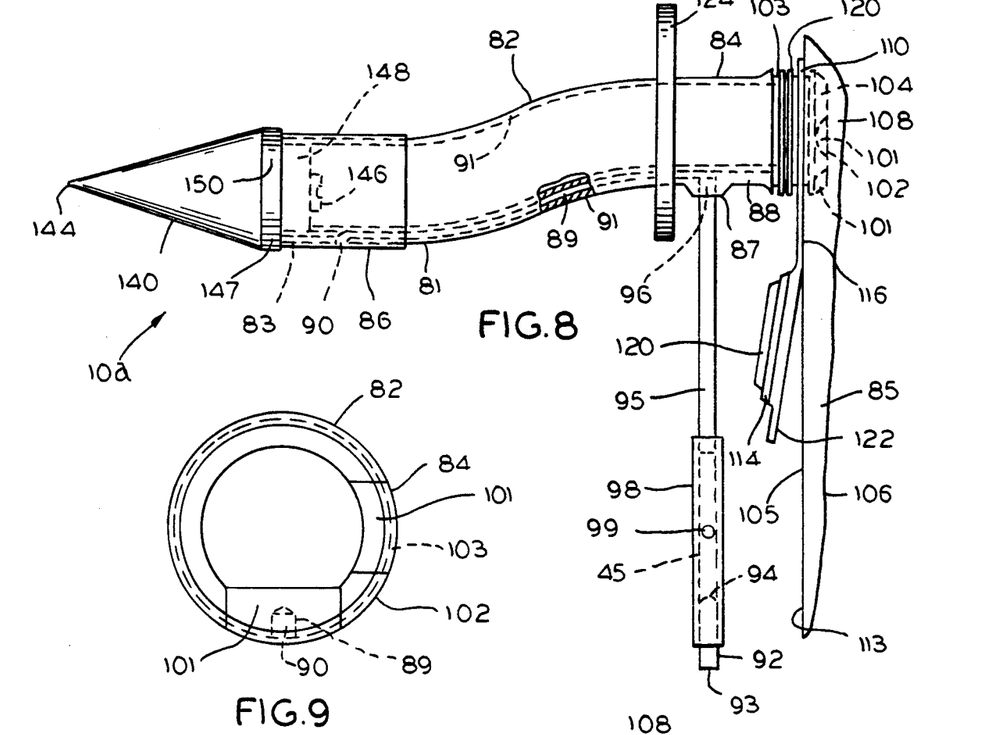
FIG. 8 is a side view of another embodiment of a temporary colostomy tube apparatus, embodying the principles of the invention, and showing the trocar removably positioned in the receiving end of the excrement tube.
FIG. 9 is an end view of the disposal end of the excrement tube in FIG. 8.

Turning now more specifically to FIG. 8, an alternate embodiment for the temporary colostomy apparatus is shown and indicated generally by the reference numeral 10 and suffix "a". The temporary colostomy apparatus 10a includes a hollow open ended excrement tube 82 having a receiving end 83 to receive the fecal stream for passage through the tube 82 to the disposal end 84 for flowing into a fecal collection bag 85. An inflatable internal balloon 86 (FIG. 17) is fused to the outside surface 81 of the excrement tube at the receiving end 83 of the tube.

An inlet opening 87 is formed in the bottom wall 88 at the disposal end 84 of the tube 12. An elongated hollow and narrow internal tubular member 89 extends from the inlet opening 87 to the inside of the internal balloon 86 via outlet 90. The tubular member 89 is fused to the inside surface 91 of the tube 82.

A one way valve 92 includes an input end 93 and an output end 94 attached to an external tubular member 95. The outlet end 96 of the external tubular member 95 is secured inside the inlet opening 87 with the internal tubular member 89 to communicate therewith. An aperture 99 is formed in the external tubular member 95 to communicate with the inside of the external balloon 98 and inflate the external balloon 98 simultaneously with the inflating of the internal balloon 86.

The external balloon 98 monitors approximately the size of the inflated internal balloon 86 to determine whether the fecal stream is being fully diverted. Liquid 51 is used to inflate the internal balloon 86 and the external balloon 98 via the external tubular member 95 and the internal tubular member 89.

Arcuate concave grooves 101 are formed in the outermost edge 102 of the disposal end 84 of the tube 82. The grooves 101 afford an additional pathway for the fecal stream even if the primary flow path out from the disposal end 84 of the tube 82 is blocked.

Figure 16:
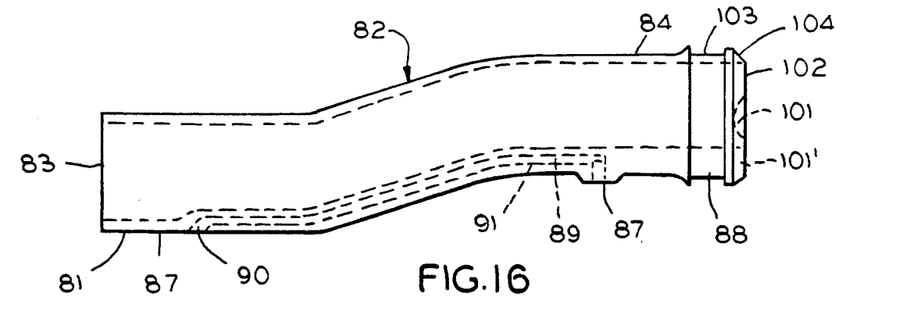
FIG. 16 is a side view of another embodiment of the excrement tube (also shown in FIG. 8)

A circular depression 103 is formed in the disposal end 84 of the tube 82 (FIG. 16). An end portion 104 of the disposal end 84 is circularly inclined outward from the outermost edge 102 to adjacent the depression 103.

Figure 10:
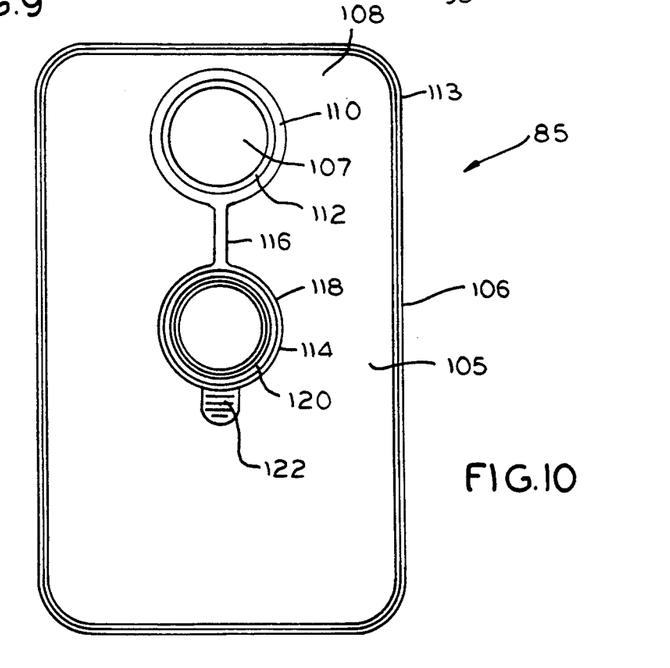
FIG. 10 is a front view of another embodiment of an excrement collection bag.

The collection bag 85 includes a front side 105, a rear side 106 and an opening 107 formed at the upper end 108 of the front side 105 of the bag 85 (FIG. 10). A circular rim 110 circumscribes the opening 107 and is sealed to the front side 105 of the bag 85. A hollow coupling ring 112 is integrally formed to the rim 110 and extends outward therefrom, and also encircles the opening 107. The inside of the ring 112 communicates with the opening 107 in the collection bag 85.

The front side 105 and rear side 106 of the bag 85 may be substantially rectangular sheets of flexible plastic material sealed together to form a continuous border or seal 113. The border 113 is more rigid than the front and rear sheets 105,106, and thus prevents the bunching together or twisting of the bag 85 which could block the flow of the diverted fecal stream.

A lid 114 fits on to the coupling ring 112 for closing the bag 85. A connecting link 116 connects the rim 110 to the lid 114. The lid 114 includes a collar 118 and an annular neck 120 spaced inward from the collar 118.

When closing the collection bag 85, the neck 120 of the lid 114 fits inside the coupling ring 112 and the coupling ring 112 snaps into the space between the collar 118 and the neck 120 of the lid 114.

When attaching the collection bag 85 to the disposal end 84 of the excrement tube 82, the coupling ring 112 slides along the inclined end portion 104 until positioning inside the annular depression 103 and the disposal end 84 of the tube 82 fits through the opening 107 in the bag 85. The attachment of the bag 85 with the tube 82 affords a tight fit association so that the fecal stream flows from the tube 82 into the collection bag 85. When the bag 85 has been sufficiently filled, the coupling ring is pulled out from the depression 103 and unto the inclined end portion 104 of the disposal end 84, and finally pulled away fom the tube 82. The lid 114 is inserted onto the coupling ring 112 to seal the bag 85 closed. A tab 122 is provided to pull the lid 114 off from the coupling ring 112, prior to inserting the bag 85 on the disosal end 84 of the tube 82.

The coupling ring 112 and the lid 114 are sufficiently flexible to afford ease in connecting and disconnecting the bag 85, and still providing a tight seal when closing the bag 85 or attaching the bag 85 to the tube 82.

Figures 11, 12:
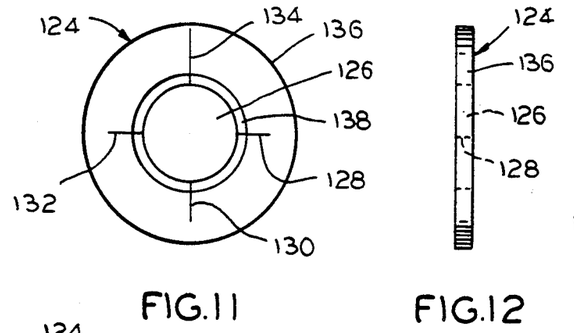
FIG. 11 is a side view of another embodiment of the retainer ring.
FIG. 12 is an end view of the retainer ring in FIG. 11.
Figure 13:
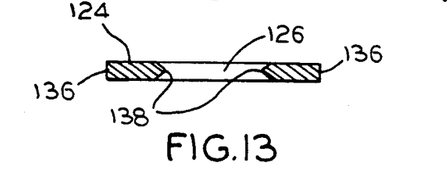
FIG. 13 is a sectional view of the retainer ring in FIG. 11, to show the circular bevelled portion of the retainer ring bordering the opening of the retainer ring.

Turning now to FIGS. 11,12 and 13, a flexible retainer ring or washer is shown and identified by the reference numeral 124. The washer 124 includes a central opening 126 and a plurality of slits 128,130,132 and 134 cut through the thickness of the washer 124 and spaced approximately ninety(90) degrees apart.

The slit 134 extends from the opening 126 to the outer periphery 136 of the washer 124. The slits 128,130 and 132 extend from the opening 126 to a point spaced from the periphery 136 of the washer 124.

The slits 128,130,132 and 134 enable the washer 124 to be easily angled or twisted or turned from one position to another, when positioned on the tube 82 to afford a tight association with the tube and also with the outside body surface of the patient without undue pressure being applied against the body of the patient. Furthermore, the washer 124 may be turned or twisted to lie substantially flat against the patient, and than secured to the tube 12 with a glue or other suitable adhesive material.

As may be seen from FIG. 13, the washer 124 includes a bevelled annular portion 138 adjacent the opening 126 to provide reduced thickness and greater flexibility. Thus, when properly positioning the tube 82, the washer 124 may be easily twisted or turned at the annular portion 138 to accommodate for the position of the tube 82 prior to securing the washer to the tube 12, thereby preventing the washer from sliding outward away from the body of the patient.

Figure 14:
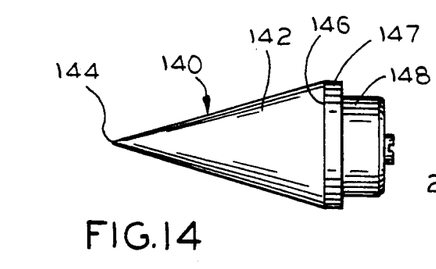
FIG. 14 is a perspective side view of another embodiment of the trocar.
Figure 15:
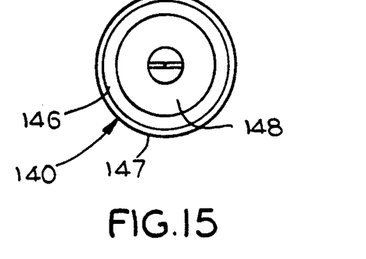
FIG. 15 is a view of the rear end of the trocar in FIG. 14 which is positioned in the receiving end of the excrement tube.

Turning now more specifically to FIGS. 14 and 15, another embodiment of a trocar is shown and indicated generally by the reference numeral 140, and comprises a conical portion 142 having a sharply pointed outer end 144. The conical portion increases in cross sectional area from the point 144 to a circular shoulder 146. A circular lip 147 borders the shoulder 146 and extends outward therefrom. An annular neck 148 is spaced inward from the circular lip 147 and also protrudes outward from the shoulder 146.

The outside diameter of the neck 148 is just slightly less than the inside diameter of the receiving end 83 of the excrement tube 82. The inside circumference of the circular lip 147 is just slightly greater than the circumference of the deflated internal balloon 86 sealed on the receiving end 83 of the tube 82. As may be seen from FIG. 8, the neck 148 of the trocar 140 press fits inside the receiving end 83 of the tube 82 and the outermost end 150 of the receiving end 83 abuts the shoulder 146 between the lip 147 and the neck 148. The circular lip 147 functions as a protective shield around the outer edge of the deflated internal balloon 86 when the trocar is positioned inside the receiving end 83 of the tube 82 for forming the opening in the abdomen and the colon 11.

Figure 17:
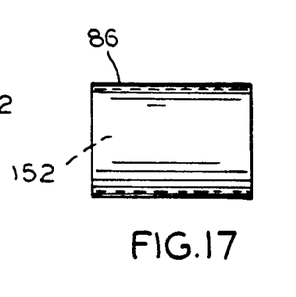
FIG. 17 is a side view of the internal balloon.
Figure 18:
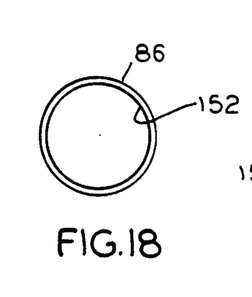
FIG. 18 is an end view of the balloon in FIG. 17.

In FIGS. 17 and 18, the internal balloon 86 is shown having a substantially cylindrical shape. The inside surface 152 of the balloon 86 fits on the receiving end 83 of the tube and is sealed thereto.

The internal balloon 86 has a greater horizontal length than the donut shaped internal balloon 26 (FIG. 1). Preferably, the horizontal length of balloon 86 is one and one-half times the internal diameter of the arrested colon at the site where the excrement tube 82 is inserted. The elongated cylindrical balloon 86 affords an abutting surface against the band 64 (with a portion of the colon sandwiched between) and also with the inside surface of the colon to prevent the tube 82 from shifting out from the path of the fecal stream.

In the event the band 64 prematurely dissolves or disintegrates (FIG. 19), the excrement tube 83 would tend to shift position and drift outwardly. If the receiving end 83 of the tube 82 would turn 90 degrees, the receiving end 83 would position against the internal colon surface, and no longer lie in the fecal pathway for diverting the fecal stream. The larger horizontal length for the internal balloon 86 (FIG. 19) provides a greater abutting or contacting surface to prevent substantial shifting of the position of the receiving end 83 of the excrement tube 82, even if the band 64 prematurely disintegrates and the tube 82 would tend to revolve or move outwardly toward the outside of the abdomen.

The balloon 26,86 may be constructed from an opaque material, or the liquid solution 51 inflating the balloon may have opaque coloring, such as an opaque colored saline solution. In this manner, an x-ray of the area would reveal whether the balloon is sufficiently inflated during use of the temporary colostomy apparatus 10,10a. The opaque coloring could be used in addition to or in place of the external monitoring balloon 48.

MODE OF OPERATION

With reference more specifically to FIGS. 1 through 4, the use of the temporary colostomy tube apparatus 10 will be described. A site on the transverse colon or sigmoid colon is selected. An incision 19 is made through the entire thickness of the abdominal wall, at a location to afford access to the selected segment of the colon. The trocar 54 removably positioned in the receiving end 14 of the excrement tube 12 is inserted through the incision 19 to form an opening in the abdominal muscle having a diameter substantially the same as the diameter of the excrement tube 12. The trocar may now be removed from the receiving end 14 of the tube 12. The mesentery is dissected away from the colon for a distance of approximately 1½ to 2 inches inward from the incision 19.

The band 64 formed of an absorbable material, which may be an absorbable polyglycolic acid mesh or an absorbable vicryl knitted mesh, is cut to a length to correspond to the circumference of the arrested colon 11 where the mesentery was disected away. The band 64 is wrapped snugly around the outside of the arrested colon to cause a slight depression therein. The ends of the band 64 are sutured together with an absorbable suture. Stool in the colon is milked proximally to the band 64 to empty the selected segment, and non-crushing bowel clamps (not shown are placed to isolate about a 4 inch length of the colon where the excrement tube 12 will be inserted.

A conventional type purse string suture is placed on the anterior surface 80 of the colon spaced outward from the band 64 but adjacent to the opening 19 formed in the abdomen. The purse string suture extends to the seromuscular layer of the colon, and is preferably formed from a non-absorbable material such as a silk suture.

A stab is made in the center of the purse string suture to form the slit opening 20, to receive the catheter 12 inserted into the colon.

The trocar 54 is removed from the receiving end 14 of the tube and the covering sheath 78, if used for a protective cover over the balloon 26, is removed. The retainer ring 52 is positioned on the receiving end 14 of the excrement tube and moved to the disposal end 16 to a position near but inward from the external tubular member 46.

The receiving end 14 of the excrement tube 12 with the balloon 26 deflated and the intermediate portion 22 of the tube 22 are inserted through the incisional opening 19 in the abdomen and the slit opening 20 in the colon 11 and into the lumen of the colon.

The internal balloon 26 is inflated with liquid 51 forced into the one way valve 38 to flow through the external tubular member 46, into the internal tubular member 32 and finally into the inside of the balloon 26 via the outlet 35. The balloon 26 is inflated to occupy the entire lumen and is slightly larger in circumference that the dissolvable band 64. Preferably, the inflated balloon causes a slight bulge 28 in the colon. As the internal balloon 26 is also being inflated the external monitoring balloon 48 is being inflated as the fluid flows through the aperture 50 in the external tubular member and through an opening into the monitoring balloon 48.

The disposal end 16 of the tube is pulled outward on the outside of the body of the patient until the inflated balloon rests at the proximal edge of the band 64 (but would be the distal edge with respect to the slit).

If the abutting contact of the balloon 26,86 with the dissolvable band 64 is not fixed and firm, less than the entire fecal stream would be diverted through the excrement tube. Fecal matter would then seep into the surgically tender areas and thereby greatly increase the probability of infection.

The purse string suture is tied securely in place around the outside of the tube to close the slit 20 around the tube 12. Anterior segments of the colon adjacent to the slit 20 are sutured to the peritoneum of the abdominal wall adjacent to the incision 19. Preferably these sutures are non-dissolvable. This snugly positions the colon against the inside of the abdominal wall to minimize movement of the tube 12 even if normal patient activity causes contact with the disposal end 16 of the tube. The bowel clamps are now removed.

The flexible retainer ring 52 is now manipulated inward on the outside of the body until it is flush with the skin to prevent inward movement of the tube 12 which would de-stabilize the contact of the internal balloon 26 and the band with the common segment of the colon, causing seepage of the fecal stream to the tender area of the colon or rectal bowel. The retainer ring 52 may be glued to the tube 12 with a silicone adhesive or other suitable adhesive. The retainer ring 52 may also be fastened to patient with adhesive strips or other suitable means.

If the washer 124 (FIG. 11) is used in place of the retainer ring 52, the slits 128, 130, 132 and 134 enable the washer 124 to be easily turned or twisted for positioning the washer 124 flush against the body of the patient even if the tube 12 is angled with respect to the abdomen, and thereafter the turned or twisted washer 124 may be taped or glued to the tube 12. Additional capability for turning and twisting the washer 124 is provided by the reduced thickness of the annular portion 138 which hugs the outside surface 27 of tube 12 (or tube 82).

After the retainer ring or washer 52 or 124 is fastened in place, the disposal bag 18 is tied on to the disposal end 16 of the tube 12. Arcuate concave grooves 74 are formed in the outermost edge 76 of the disposal end 16 of the tube 12 to afford an outlet flow path in the event the bag 18 bunches up or the neck 70 of the disposal bag 18 bends to the side and blocks the main outlet opening. Alternatively, the snap on fecal collection bag 85 which does not have a neck and has a studier rectangular border, may be used, and would not cause fecal flow blockage.

After the colostomy apparatus 10,10a has been in place for about 21 days, the balloon 26,86 is deflated and the excrement tube 22,82 removed. The band 64 remains inside the body of the patient after the 21 day period, to dissolve and disintegrate over time.

Various modifications of the invention of a temporary colostomy apparatus described herein, are within the spirit and scope of the invention, the scope of which is limited solely and defined by the appended claims.

1. A temporary colostomy apparatus for inserting through an incision in the abdomen and a slit in the colon of the patient to divert the fecal stream, said apparatus comprising:

a hollow excrement tube for positioning inside the colon after passing through said incision in the abdomen and said slit in the colon, said tube having a receiving end and a disposal end including an outer edge, said fecal stream passing from said receiving end to said disposal end of the tube;

an inflatable balloon secured to the outside of said receiving end of the tube, said balloon being inflated to contact the inside surface of the colon so that said tube and the inflated balloon block the fecal stream inside the colon for diverting the fecal stream into the receiving end of the tube;

a band for wrapping around the outside of the colon between said balloon and said slit in the colon, said inflated balloon having a larger circumference than the band and being positioned adjacent to said band in an abutting relationship to sandwich a common segment of said colon therebetween and thereby preventing said tube from moving outward toward said slit, the material forming said band dissolving after a period of time in the body; and dissolvable sutures for securing the band around the colon.

2. The temporary colostomy apparatus of claim 1, wherein said absorbable material for the band is polyglycolic acid mesh.

3. The temporary colostomy apparatus of claim 1 includes:

an internal fluid passageway extending from the disposal end to the receiving end of the tube and communicating with said balloon; and an external fluid passageway communicating with said internal fluid passageway and positioned on the outside of the body of the patient, so that fluid flows from the external passageway to the internal passageway for inflating the balloon.

4. The temporary colostomy apparatus of claim 3 includes:

a monitoring balloon positioned on the outside of the body in communication with the external passageway to inflate simultaneously with the inflating of the first mentioned balloon and to deflate simultaneously with the deflating of the first mentioned balloon.

5. The temporary colostomy apparatus of claim 3 includes:
   an input into said external fluid passageway;
   a one way valve is interposed between said input and said external fluid passageway to permit fluid to flow into the external fluid passageway and block back flow from the external fluid passageway and out from said input.

6. The temporary colostomy tube of claim 4, wherein said external fluid passageway is a hollow tubular member, said monitoring balloon being secured on said tubular member, said tubular member having an aperture aligned with an opening formed in said monitoring balloon to communicate with the monitoring balloon so that a portion of the fluid flow is utilized for inflating the monitoring balloon.

7. The temporary colostomy apparatus of claim 1, wherein the material of said band is excretable from the body of the patient.

8. The temporary colostomy tube apparatus of claim 1 includes:
   a flexible washer having a central opening for receiving the disposal end of the tube for preventing inward movement of the tube, said washer including means for adjusting the position of the washer.

9. The temporary colostomy apparatus of claim 1, wherein said internal balloon inflates to a substantially cylindrical shape.

10. The temporary colostomy apparatus of claim 1, wherein the length of said internal balloon at said receiving end of the tube is greater than the diameter of the arrested colon where said excrement tube is inserted.

11. A temporary colostomy apparatus for inserting through an incision in the abdomen and a slit in the colon to divert the fecal stream, said apparatus comprising:
   a hollow excrement tube for positioning inside the colon after passing through said incision in the abdomen and said slit in the colon, said tube having a receiving end and a disposal end for passing said fecal stream from said receiving end to said disposal end on the outside of the body;
   an internal inflatible balloon secured to the outside of said receiving end of the tube, said internal balloon being inflated to contact the inside surface of the colon so that said tube and the inflated balloon block the fecal stream inside the colon for diverting the fecal stream into the receiving end of the tube;
   a band for wrapping around the outside of the colon between said balloon and said slit in the colon, said inflated balloon having a larger circumference than the band and being positioned adjacent to said band in an abutting relationship to sandwich a common segment of said colon therebetween and thereby preventing said tube from moving outward toward said slit, said band being formed of a material to dissolve after a period of time in the body; and
   a removable sheath for covering said balloon to protect said balloon, prior to operatively positioning said tube inside the colon.

12. A temporary colostomy apparatus for inserting through an incision in the abdomen and a slit in the colon of the patient to divert the fecal stream, said apparatus comprising:
   a hollow excrement tube for positioning inside the colon after passing through said incision in the abdomen and said slit in the colon, said tube having a receiving end and a disposal end including an outer edge, said fecal stream passing from said receiving end to said disposal end of the tube;
   an inflatable balloon secured to the outside of said receiving end of the tube, said balloon being inflated to contact the inside surface of the colon so that said tube and the inflated balloon block the fecal stream inside the colon for diverting the fecal stream into the receiving end of the tube;
   a band for wrapping around the outside of the colon between said balloon and said slit in the colon, said inflated balloon having a larger circumference than the band and being positioned adjacent to said band in an abutting relationship to sandwich a common segment of said colon therebetween and thereby preventing said tube from moving outward toward said slit, the material forming said band dissolving after a period of time in the body;
   at least one groove formed inward from the outer edge of the disposal end of the tube; and
   a disposal bag for positioning on the disposal end of the tube, said groove providing a pathway into the disposal bag when said bag is bent and blocks the flow of the fecal stream out from the disposal end of the tube.

13. A method for diverting the fecal stream in the colon of the patient using a colostomy apparatus including an excrement tube having a receiving end and a disposal end, an inflatable balloon disposed at the receiving end of the tube, and a sheet of material dissolvable in the body of the patient, said method comprising the steps of:
   making an incision in the abdomen at a predetermined location to gain entry into the abdominal cavity;
   wrapping said dissolvable sheet material around the outside of the colon to form a band at a desired location spaced from an area on the colon selected to be slit open;
   slitting the colon open at said area;
   inserting said excrement tube through said incision and said slit and into the lumen of the colon, so that the balloon is spaced a greater distance from the slit than said band;
   inflating said balloon so that the outer periphery of the balloon contacts the inside surface of the colon; and
   positioning the tube so that the inflated balloon abuts said band with a common segment of the colon therebetween, to prevent outward movement of the balloon toward said slit, said tube and inflated balloon blocking the fecal stream to divert the fecal stream into the receiving end of the tube for passage through the tube to be discharged from said disposal end;
   securing the disposal end of the tue to the outside of the body of the patient to prevent movement of the tube further inside the colon and away from the slit opening; and
   deflating said balloon and removing said tube from the colon and the body of the patient during a predetermined time period after the band has been positioned inside the body of the patient, said time period being prior to any substantial dissolving of said band.

14. The method of claim 13 includes:
sensing when said first balloon deflates to indicate that the fecal stream is not being fully diverted through the tube.

15. The method of claim 14, includes:
inflating a monitoring balloon on the outside of the body simultaneously with the inflating of said first mentioned balloon; and
deflating the monitoring balloon when said first mentioned balloon is being deflated.

16. The method of claim 13, wherein said apparatus includes a flexible retainer ring for positioning on the disposal end of the excrement tube, and said method further comprising:
bending said retainer ring so that the front side of the ring is substantially flat against the outside of the abdomen; and
securing said bent retainer ring against said abdomen.

17. The method of claim 13, wherein said tube is removed from the body after 14 days from the date said band is wrapped around the colon.

18. The method of claim 13, wherein said band is formed from a polyglycolic acid mesh.

19. A method for diverting the fecal stream in the colon of the patient using a colostomy apparatus including an excrement tube having a receiving end and a disposal end, an inflatible internal balloon disposed at the receiving end of the tube, and a sheet of material dissolvable in the body of the patient, said method comprising the steps of:
making an incision in the abdomen at a predetermined location to gain entry into the abdominal cavity;
wrapping said dissolvable sheet material around the outside of the colon to form a band at a desired location paced form an area on the colon selected to be slit open;
slitting the colon open at said area;
inserting said excrement tube through said incision and said slit and into the lumen of the colon, so that the balloon is spaced a greater distance from the slit than said band;
attaching a segment of the colon adjacent to said slit in the colon to the abdominal wall adjacent to the abdominal incision after the excrement tube has been positioned in the colon;
inflating said internal balloon so that the outer periphery of the balloon contacts the inside surface of the colon; and
positioning the tube so that the inflated balloon abuts said band with a common segment of the colon therebetween, to prevent outward movement of the balloon toward said slit, said tube and inflated balloon blocking the fecal stream to divert the fecal stream into the receiving end of the tube for passage through the tube to be discharged from said disposal end;
securing the disposal end of the tube to the outside of the body of the patient to prevent movement of the tube further inside the colon and away from the slit opening; and
deflating said internal balloon and removing said tube from the colon and the body of the patient before any substantially dissolving of said band.

20. A method for diverting the fecal stream in the colon of the patient using a colostomy apparatus including an excrement tube having a receiving end and a disposal end, an inflatable balloon disposed at the receiving end of the tube, and a sheet of material dissolvable in the body of the patient, said method comprising the steps of:
making an incision in the abdomen at a predetermined location to gain entry into the abdominal cavity;
wrapping said dissolvable sheet material around the outside of the colon to form a band at a desired location spaced from an area on the colon selected to be slit open;
slitting the colon open at said area;
inserting said excrement tube through said incision and said slit and into the lumen of the colon, so that the balloon is spaced a greater distance from the slit than said band;
inflating said balloon with an opaque solution so that the outer periphery of the balloon contacts the inside surface of the colon; and
positioning the tube so that the inflated balloon abuts said band with a common segment of the colon therebetween, to prevent outward movement of the balloon toward said slit, said tube and inflated balloon blocking the fecal stream to divert eh fecal stream into the receiving end of the tube for passage through the tube to be discharged from said disposal end;
securing the disposal end of the tube to the outside of the body of the patient to prevent movement of the tube further inside the colon and away from the slit opening; and
deflating said internal balloon and removing said tube from the colon and the body of the patient before any substantial dissolving of said band.

21. A temporary colostomy apparatus for inserting through an incision in the abdomen and a slit in the colon of the patient to divert the fecal stream, said apparatus comprising:
a hollow excrement tube for positioning inside the colon after passing through said incision in the abdomen and said slit in the colon, said tube having a receiving end and a disposal end including an outer edge, said fecal stream passing from said receiving end to said disposal end of the tube;
an inflatible balloon secured to the outside of said receiving end of the tube, said balloon being formed from an opaque material, said balloon being inflated to contact the inside surface of the colon so that said tube and the inflated balloon block the fecal stream inside the colon for diverting the fecal stream into the receiving end of the tube; and
a band for wrapping around the outside of the colon between said balloon and said slit int eh colon, said inflated balloon having a larger circumference than the band and being positioned, adjacent to said band in an abutting relationship to sandwich a common segment of said colon therebetween and thereby preventing said tube from moving outward toward said slit, the material forming said band dissolving after a period of time in the body.

22. A method for diverting the fecal stream in the colon of the patient using a colostomoy apparatus including an excrement tube having a receiving end and a disposal end, an inflatible internal balloon disposed at the receiving end of the tube, and a sheet of material dissolvable in the body of the patient, said sheet having opposite ends, said method comprising the steps of:
making an incision in the abdomen at a predetermined location to gain entry into the abdominal cavity;

wrapping said dissolvable sheet material around the outside of the colon to form a band at a desired location spaced from an area on the colon selected to be slit open;

attaching said opposite ends of the sheet with dissolvable sutures;

slitting the colon open at said area;

inserting said excrement tube through said incision and said slit and into the lumen of the colon, so that the balloon is spaced a greater distance from the slit than said band;

inflating said internal balloon so that the outer periphery of the balloon contacts the inside surface of the colon; and positioning the tube so that the inflated balloon abuts said band with a common segment of the colon therebetween, to prevent outward movement of the balloon toward said slit, said tube and inflated balloon blocking the fecal stream to divert the fecal stream into the receiving end of the tube for passage through the tube to be discharged from said disposal end;

securing the disposal end of the tube to the outside of the body of the patient to prevent movement of th tube further inside the colon and away from the slit opening; and deflating said internal balloon and removing said tube from the colon and the body of the patient before any substantial dissolving of said band.

* * * * *